United States Patent [19]

Lazarus et al.

[11] 4,391,276
[45] Jul. 5, 1983

[54] PERITONEAL CATHETER

[76] Inventors: Harrison Lazarus, 1474 Penrose Dr., Salt Lake City, Utah 84103; James A. Nelson, 1708 Forest Hills Dr., Salt Lake City, Utah 84106

[21] Appl. No.: 217,127

[22] Filed: Dec. 16, 1980

[51] Int. Cl.³ ............................................. A61M 25/00
[52] U.S. Cl. .................................... 604/266; 128/350; 128/213 A
[58] Field of Search ............... 128/349, 350, 348, 347, 128/214, 213 A

[56] References Cited

U.S. PATENT DOCUMENTS

| Re. 27,310 | 3/1972 | Hakim | 128/350 |
| 3,136,316 | 6/1964 | Beall | 128/350 R |
| 3,314,430 | 4/1967 | Alley et al. | 128/350 R |
| 3,459,188 | 8/1969 | Roberts | 128/347 |
| 4,291,694 | 9/1981 | Chai | 128/347 X |

Primary Examiner—Stephen C. Pellegrino
Attorney, Agent, or Firm—Trask & Britt

[57] ABSTRACT

A safer peritoneal catheter with improved non-plugging characteristics is disclosed. The catheter has very fine sidewall openings which generally have projections associated therewith which tend to prevent the openings from becoming clogged with tissue. The catheter and side holes are sized to facilitate removal of blood and liquids from the peritoneal cavity. The very fine sidewall openings enhance the reliability of the catheter while permitting it to have excellent strength and resistance to breakage.

5 Claims, 6 Drawing Figures

PERITONEAL CATHETER

BACKGROUND OF THE INVENTION

1. Field:

This invention relates to catheters or cannulae useful in extracting fluids from the peritoneal cavity.

2. Prior Art:

Catheters and cannulae suitable for removing fluids from the peritoneal cavity are described in U.S. Pat. No. 4,128,173, issued to Lazarus and Nelson.

Another type of peritoneal catheter is described in U.S. Pat. No. 3,459,188 to Roberts.

These prior catheters have sidewall openings which communicate with a central or axial bore to permit fluids external to the catheter, e.g., fluids within the abdominal cavity, to be drawn through the sidewall openings into the central bore and thereafter withdrawn from one end of the catheter which is external to the abdominal cavity. Generally, the sidewall openings of prior catheters are relatively large in relation to the thickness of the catheter, e.g., the Roberts patent at Col. 2, lines 92, et. seq. describes sidewall openings of 0.01 inch to 0.025 inch in diameter.

Previous catheters work well except when tissue clogs the sidewall openings, as may happen when a catheter (or cannula) is inserted through the peritoneum, for example, or when tissue is drawn into the opening. Also, the relatively large openings in the sidewall of a catheter tend to weaken the device. Although catheter breakage has not been a problem, any breakage inside a patient would require surgical removal of the broken part.

OBJECTS OF THE INVENTION

It is an object of the instant invention to provide a non-plugging catheter.

It is another object of the instant invention to provide a non-plugging catheter which is easily inserted and removed through tissue.

A further object of the instant invention is to provide a catheter which does not injure tissue which it passes through.

Another object of the instant invention is to provide catheters with strong, porous sidewalls.

DESCRIPTION OF THE INVENTION

Figure 1:
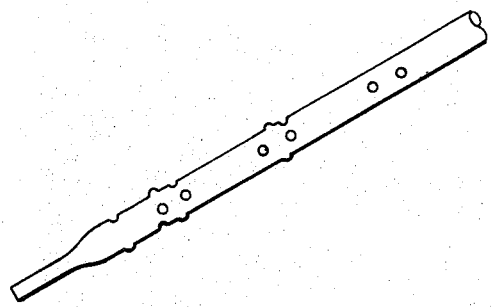
FIG. 1 is an elevational side view of an improved, non-plugging catheter having sidewall protrusions proximate to sidewall openings.

A cannula or catheter with non-plugging characteristics has been invented. The cannula comprises a hollow tubular member with an opening on at least one end. Very fine sidewall openings are spaced circumferentially and longitudinally along the tubular member. A substantial number of the sidewall openings have a protrusion associated. The protrusion may have substantially any shape. The cannula is particularly useful in peritoneal lavage and dialysis techniques.

The cannula has a length of from about 75 to 300 millimeters, preferably a length of about 100 to 250 millimeters, an external diameter of from about two to about four millimeters and an interior diameter of from about 1.0 to about 3.5 millimeters. Typical sidewall openings for a cannula of the instant invention have diameters of from about 0.01 to about 2.0 millimeters.

Sidewall openings of a diameter of less than about 0.1 millimeter, and especially less than about 0.05 millimeter, have been found to be non-clogging even when no protrusion has been associated therewith. Although larger openings, e.g., ones having a diameter of 1.0 millimeter or greater have been found clogged with tissue from the omentum, apparently caused by tissue in contact with the external surface of the catheter being sucked into the opening during extraction of fluids from the peritoneum, catheters containing small sidewall openings did not experience plugging whem in peritoneal lavage and dialysis procedures.

Protrusions are desirable even with very minute sidewall openings (0.01 to 0.1 millimeters) and especially effective with small openings (less than about 2.0 millimeters and preferably less than about 0.5 millimeters). Thus, the presence of protrusions on the external surface of the catheter in the vicinity of the sidewall openings tends to keep tissue in contact with the external surface of the catheter sufficiently far away from the sidewall opening to prevent it from becoming clogged.

The protrusions need not be overly large to be effective. Protrusions projecting a distance of about 0.01 to about 1.0 millimeter from the exterior surface are particularly useful. Larger protrusions may be utilized, however, such protrusions may cause some patient discomfort as the catheter is inserted in or withdrawn from the peritoneal cavity. Thus, the smallest effective protrusion is generally preferred.

The size of the protrusion generally varies proportionally with the size of the sidewall opening it is protecting. A small opening can be protected by a small protrusion. For sidewall openings of less than about 0.05 millimeter, protrusions having a height of 0.1 millimeter, or even less, are effective.

A catheter may have from about six to about 100, or more, sidewall openings. Maximum non-plugging characteristics are achieved when each opening is protected by a protrusion. However, the invention is effective when only a portion of the sidewall openings are so protected.

Typical protrusions project from the exterior sidewall about 0.01 to about 1.0 millimeter. The length of the protrusion along the sidewall is not considered to be critical for most purposes. The height or depth of protrusions can vary considerably although extra large protrusions could cause patient discomfort or trauma during insertion and removal of the cannula. Smooth surfaced protrusions are preferred.

Protrusions can be formed in a first sidewall by passing a fine needle through the opposite sidewall with sufficient force to dimple the interior of the first sidewall as it punctures the sidewall. Thus, a small node or nodule is formed on the external surface of the first sidewall surrounding the opening in that sidewall. This manner of making the side holes produces external protrusions on half of the holes. Protrusions may be formed about each sidewall opening by the use of a needle wherein each has a slight barb near its end. Such needles are used to puncture only one sidewall. As the needles are withdrawn, the barb will tend to flip the rim of the sidewall opening outward so that a projection or protrusion is formed as part of the opening.

The location of protrusions with respect to sidewall openings is important. A protrusion intended to protect a certain sidewall opening is proximate to the opening and is preferably adjacent to said opening. Although the protrusion need not be located adjacent to the opening it is protecting to be effective, it should be sufficiently close to prevent tissue from being drawn into the opening. The size of the protrusion may affect its location; i.e., a larger protrusion may effectively protect an opening without being adjacent thereto.

Although the invention has thus far been described as a cannula, which usually means a plastic or polymeric device associated with a sharp, elongated member which fits within the hollow bore of the cannula, the invention is applicable to any hollow, tubular member which penetrates the flesh and which has sidewall openings which can be clogged by occluded tissue. Thus, hollow steel needles with small, protected sidewall openings are contemplated as being within the scope of the invention.

Further description of the invention may be facilitated by reference to the attached drawings. FIG. 1 illustrates one embodiment of the instant invention wherein a thin-walled, hollow, tubular member 10 has a smaller insertion end 11 which precedes the remainder of the device through tissue. A distal end 12 is usually located external to the patient in whom the device is inserted.

The device of FIG. 1 has very small sidewall openings 13 situated in a spiral fashion along a substantial length of the device. The sidewall openings can be situated in a spiral, linear or other convenient pattern. The spiral pattern of the openings has regular spacing so that a needle passed through one sidewall opening, e.g., 13a, can be forced against the opposite sidewall to form a protrusion 13b with an opening therein. Half the openings of a device made in this fashion are without protecting protrusions.

Figure 2:
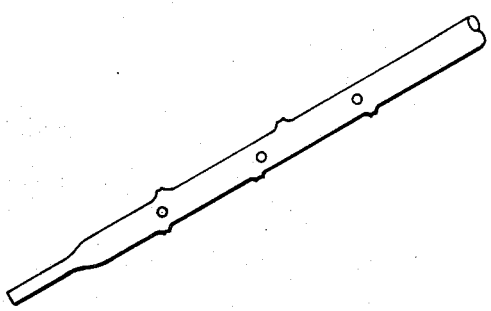
FIG. 2 is an elevational side view of a non-plugging catheter having sidewall protrusions encircling said sidewall openings.

The device illustrated in FIG. 2 has protrusions in close proximity to each sidewall opening. The openings and associated protrusions 14 are shown located in a spiral order along the length of the cannula. The structure of the combination of protrusion and opening is shown magnified in FIG. 2a.

Figure 2A:
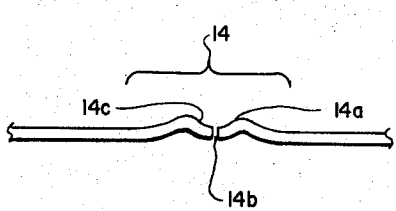
FIG. 2a is an enlarged view of the protrusion and sidewall opening of the device illustrated in FIG. 2.

The protrusions 14a of FIG. 2a encircles the sidewall opening 14b similar to the rim of a volcano encircling a crater. The opening 14b preferably is smaller than the crater 14c. Alternatively, the protrusion may be discontinuous with the protrusion forming two projections, one above and one below the sidewall opening. (In reference to the cannula, "below" indicates a position nearer the insertion end while "above" means a position closer to the extraction end.)

The combination protrusion and sidewall opening of FIG. 2a may be formed in a plastic cannula, for example, by warming the plastic, pressurizing the interior of the cannula while the sidewalls are supported by a mold. A vacuum can then be drawn on the exterior sidewall at each site where a protrusion is desired. A protrusion so formed may be indented with a flat rod to form a crater. The sidewall opening may then be made with a fine needle or stylus, either while the plastic is warm or after it is cool. Other techniques, including those described hereinabove, may be used to form the combination protrusion-sidewall opening.

Figure 3:
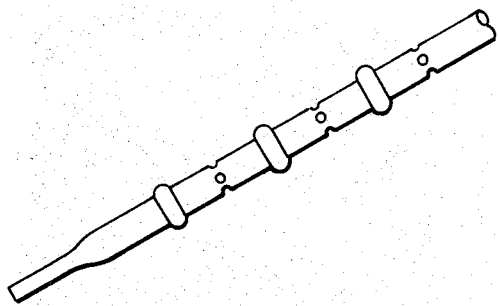
FIG. 3 is an elevational side view of a non-plugging catheter having ring-like protrusions longitudinally spaced along the catheter sidewall.

Ring-type protrusions 15 are illustrated in FIG. 3. These protrusions are continuous rings, encircling the external surface of the device. The ring protrusions are spaced longitudinally along the length of the device. Sidewall openings 16 are located in spaced circles, generally about three to five openings per circle. Generally, only one circle of openings are formed per protrusion ring, although the ring would protect a double circle of openings on each side of the ring. The cross-sectional shape of a protrusion ring is generally a segment of a circle.

Figure 4:
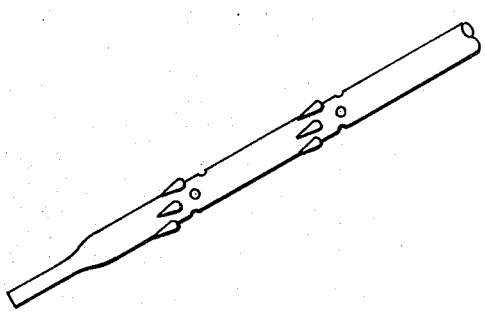
FIG. 4 is an elevational side view of a non-plugging catheter having teardrop-shaped protrusions associated with each sidewall opening.

The device of FIG. 4 has teardrop-shaped protrusions 17 located in a spiral pattern along the length of a cannula. Sidewall openings 18 are also located in a spiral pattern, preferably in the same pattern as the protrusions but displaced slightly longitudinally therefrom.

The teardrop protrusions 17 have their narrow ends pointed towards the insertion end of the cannula. The other end of the protrusion is rounded. The narrow end of a teardrop protrusion parts the flesh easily and without any danger of tearing the flesh during insertion of the cannula. The relatively abrupt termination of the protrusion adjacent to the sidewall opening ensures that any crease formed in the flesh will not collapse and cause plugging of the sidewall opening. The rounded end of the protrusion close to the sidewall opening enables the cannula to be easily withdrawn.

Cannulae illustrated in FIGS. 1 to 4 retain flexibility within the peritoneal cavity even though the sidewall openings have protective protrusions associated therewith.

Figure 5:
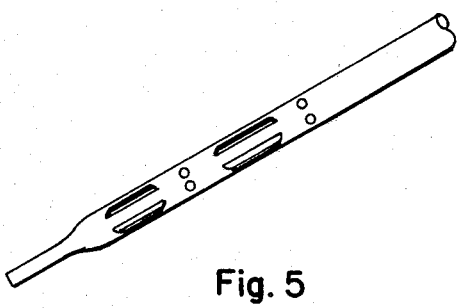
FIG. 5 is a perspective view of a cannula with longitudinal spine-like protrusions.

The device illustrated in FIG. 5 has spine-like protrusions with rounded ends. The sidewall openings are located between aligned spines. The spines are extremely effective in preventing clogging of sidewall openings, however, the spines may tend to reduce slightly the flexibility of the device. The spines may be linear or spiral in arrangement.

The cannulae of the instant invention are particularly advantageous. A strong sidewall is maintained through the use of very fine sidewall openings spaced circumferentially and longitudinally from one another. The openings are generally protected by associated protrusions to render them non-clogging. The protrusions are shaped and sized so that there is minimum damage to flesh which is contacted during insertion or withdrawn of the cannulae. Generally, the sidewall openings are round or circular in shape, although oblong or other shapes of openings may be used.

The invention described herein is particularly effective in improving the strength and non-plugging character of peritoneal catheters, or other catheters in which the external surface of the catheter may be in contact with tissue which can be drawn into the sidewall openings. The exact mechanism of clogging of larger sidewall openings is not exactly understood, but it apparently involves surface tissue, e.g., of the omentum, being drawn into the sidewall opening during withdrawal or extraction of fluids through the catheter. This surface tissue then remains in the sidewall opening even when fluids are introduced through the catheter into the peritoneum or other cavity. The reduced size of the sidewall opening has been found very effective in combating the plugging problem, especially when used in conjunction with external protrusions.

We claim:

1. A catheter comprising:

a thin-walled, hollow-bore tubular member having an opening on an extraction end, said tubular member having a hollow-bore diameter of from about 1.0 to about 3.5 millimeters and an external diameter of from about 2.0 to about 4.0 millimeters;

a plurality of sidewall openings in said tubular member, said openings having protrusions associated therewith protruding from the exterior sidewall, at least a substantial portion of said protrusions being longitudinally aligned with a substantial portion of said sidewall openings, said sidewall openings having a diameter of from about 0.01 to about 2.0 millimeters and said sidewall protrusions project from about 0.01 to about 1.0 millimeter from the exterior wall surface.

2. The catheter of claim 1 wherein said sidewall openings each have a substantially smaller cross-sectional area than the cross-sectional area of the longitudinal opening of the hollow-bore member.

3. The catheter of claim 1 wherein at least six to 100 sidewall openings are present.

4. The catheter of claim 1 wherein said tubular member has a length of from about 10 millimeters to about 25 millimeters.

5. The catheter of claim 1 wherein said protrusions substantially encircles at least a portion of said sidewall openings.

* * * * *